(12) United States Patent
Wisniewski et al.

(10) Patent No.: US 8,883,965 B2
(45) Date of Patent: Nov. 11, 2014

(54) COMPOUNDS

(75) Inventors: Kazimierz Wisniewski, San Diego, CA (US); Robert Felix Galyean, Escondido, CA (US)

(73) Assignee: Ferring B.V., Hoofddorp (NL)

( * ) Notice: Subject to any disclaimer, the term of this patent is extended or adjusted under 35 U.S.C. 154(b) by 1845 days.

(21) Appl. No.: 12/223,654

(22) PCT Filed: Feb. 5, 2007

(86) PCT No.: PCT/US2007/003213
§ 371 (c)(1),
(2), (4) Date: Mar. 23, 2009

(87) PCT Pub. No.: WO2007/095021
PCT Pub. Date: Aug. 23, 2007

(65) Prior Publication Data
US 2009/0275522 A1 Nov. 5, 2009

Related U.S. Application Data

(60) Provisional application No. 60/771,870, filed on Feb. 10, 2006.

(51) Int. Cl.
| | | |
|---|---|---|
| A61K 38/12 | (2006.01) | |
| A61K 38/11 | (2006.01) | |
| A61K 38/08 | (2006.01) | |
| A61K 38/00 | (2006.01) | |
| C07K 7/16 | (2006.01) | |
| C07K 7/06 | (2006.01) | |

(52) U.S. Cl.
CPC .... *C07K 7/16* (2013.01); *C07K 7/06* (2013.01)
USPC ........ 530/328; 514/10.9; 514/21.6; 514/15.6; 514/20.8; 514/1.1

(58) Field of Classification Search
None
See application file for complete search history.

(56) References Cited

U.S. PATENT DOCUMENTS

| | | | |
|---|---|---|---|
| 3,352,843 | A | 11/1967 | Boissonnas et al. |
| 4,483,794 | A | 11/1984 | Barth et al. |
| 4,829,051 | A | 5/1989 | Cort et al. |
| 5,459,236 | A | 10/1995 | Aurell et al. |
| 5,516,795 | A | 5/1996 | Dellaria et al. |
| 6,262,021 | B1 | 7/2001 | Uvnas-Moberg et al. |
| 6,852,697 | B1 | 2/2005 | Mathison et al. |
| 8,148,319 | B2 * | 4/2012 | Wisniewski et al. ............ 514/1.1 |
| 8,222,202 | B2 * | 7/2012 | Laporte et al. ................. 514/1.5 |
| 2003/0109670 | A1 | 6/2003 | Olivera et al. |
| 2004/0009550 | A1 | 1/2004 | Moll et al. |
| 2004/0229798 | A1 | 11/2004 | Landry et al. |
| 2009/0054309 | A1 * | 2/2009 | Wisniewski et al. ............ 514/11 |
| 2009/0275522 | A1 * | 11/2009 | Wisniewski et al. ............ 514/15 |
| 2011/0237494 | A1 | 9/2011 | LaPorte et al. |
| 2012/0196808 | A1 * | 8/2012 | Wisniewski et al. ......... 514/15.6 |

FOREIGN PATENT DOCUMENTS

| | | |
|---|---|---|
| CS | 235151 | 2/1987 |
| CS | 242062 | 2/1988 |
| EP | 1027067 | 9/2004 |
| EP | 1406649 | 2/2008 |
| GB | 1 076 984 | 7/1967 |
| RU | 2063979 | 7/1996 |
| RU | 2342949 | 1/2009 |
| WO | WO 88/01163 | 2/1988 |
| WO | WO 89/03393 | 4/1989 |
| WO | WO 91/13092 | 9/1991 |
| WO | WO 99/46283 | 9/1999 |
| WO | WO 02/064740 | 8/2002 |
| WO | WO 03/082334 | 10/2003 |
| WO | WO 03/099862 | 12/2003 |
| WO | WO 2004/030524 | 4/2004 |
| WO | WO 2006/020491 | 2/2006 |
| WO | WO 2007/095021 | 8/2007 |
| WO | WO2007/144768 | 12/2007 |

OTHER PUBLICATIONS

Vilhardt et al. Antidiuretic activity and release of factor VIII by vasopressin analogs. European Journal of Pharmacology (1993), 232(2-3), 223-6 (available online PubMed).*
Altura et al. Structure-activity basis for vasotropic peptide therapy in shock. Advances in Experimental Medicine and Biology (1972), 21, 399-408. (available online PubMed).*
Altura et al. Microcirculatory actions of polypeptides and their use in the treatment of experimental shock. Advances in Experimental Medicine and Biology (1970), 8, 239-47 (available online PubMed).*
Calabi et al. (Magnetic Resonance in Chemistry; 2005; 43(8); 654-657; ISSN 0749-1581, especially p. 655) (cited in r/t PCTUS07/003213 and efiled Aug. 6, 2008).*
Vilhardt et al. Antidiuretic activity and release of factor VIII by vasopressin analogs. European Journal of Pharmacology (1993), 232(2-3), 223-6.*
Altura et al. Structure-activity basis for vasotropic peptide therapy in shock. Advances in Experimental Medicine and Biology (1972), 21, 399-408.*

(Continued)

*Primary Examiner* — Maury Audet
(74) *Attorney, Agent, or Firm* — Fish & Richardson P.C.

(57) ABSTRACT

The present invention relates to novel compounds, pharmaceutical compositions comprising the same, use of said compounds for the manufacture of a medicament for treatment of inter alia shock conditions as well as to a method for treatment of said conditions, wherein said compounds are administered. The compounds are represented by the general formula (I), as further defined in the specification.

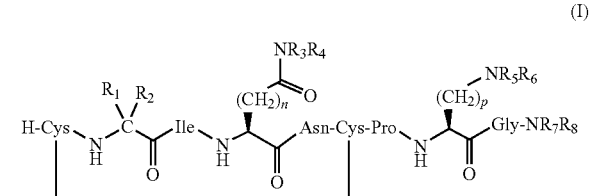

(I)

19 Claims, No Drawings

(56) References Cited

OTHER PUBLICATIONS

International Preliminary Report on Patentability and Written Opinion dated Aug. 12, 2008 for International Appln. No. PCT/US2007/003213 (7 pgs.).*
http://en.wikipedia.org/wiki/Terlipressin.*
http://en.wikipedia.org/wiki/Vasopressin.*
http://en.wikipedia.org/wiki/Cardiopulmonary_resuscitation.*
Ruiz-del-Arbol et al. Paracentesis-induced circulatory dysfunction: mechanism and effect on hepatic hemodynamics in cirrhosis. Gastroenterology. Aug. 1997;113(2):579-86.*
Calabi, H.; "H and C spectral assignments of an oxytocin-DTPA derivative, a ligand for potential receptor-specific MRI contrast agents"; Magn. Reson. Chem. 2005; vol. 43, pp. 654-657.
Altura et al., "A Structure-Activity Basis for Vasotropic Peptide Therapy in Shock", *Adv. Exp. Med. Biol.*, 1972, 21, 399-408.
Altura et al., "Microcirculatory Actions of Polypeptides and Their Use in the Treatment of Experimental Shock", *Adv. Exp. Med. Biol.*, 1970, 8, 239-247.
Barlos et al,, "Solid phase synthesis using trityl type side chain protecting groups", *Peptides*, 1992, 283-284.
Bisello et al., "Parathyroid Hormone-Receptor Interactions Identified Directly by Photocross-linking and Molecular Modeling Studies", *J. Biol. Chem.*, 1998, 273, 22498-22505.
Bodanski et al., "Synthesis of Arginine-Containing Peptides through their Ornithine Analogs. Synthesis of Arginine Vasopressin, Arginine Vasotocin, and L-Histidyl-L-phenylalanyl-L-arginyl-L-tryptophylglycine", *J. Am. Chem. Soc.*, 1964, 86(20), 4452-4459.
Boss et al., "Induction of NFAT-mediated Transcription by $G_q$-coupled Receptors in Lymphoid and Non-lymphoid Cells", *J. Biol. Chem.*, 1996, 271(18), 10429-10432.
Chen, P., "Vasopressin: New Uses in Critical Care", Southwestern Internal Medicine Conference, *The American Journal of the Medical Sciences*, 2002, 324(3), 146-154.
European Patent Office, Supplementary European Seach Report and Opinion, 13 pp., dated Nov. 24, 2010.
Fukuyama et al., "2- and 4-Nitrobenzenesulfonamides: Exceptionally Versatile Means for Preparation of Secondary Amines and Protection of Amines", *Tetrahedron Lett.*, 1995, 36, 6373-6374.
Grzonka et al., "Study of Pituitary Hormone Analogs for their Inhibitory Properties and Resistance to Carboxyamidopeptidases: [9-L-Proline]oxytocin, [9-L-Glutamic acid]oxytocin, and [8-L-Lysine,9-glycine methylamide]oxytocin", *J. Med. Chem.*, 1974, 17(12), 1294-1298.
Guild et al., "Interactions between neural and hormonal mediators of renal vascular tone in anaesthetized rabbits", *Exp. Physiol.*, 2003, 88(2), 229-241.
Hugenin et al., "Synthèse de l'Orn8-vasopressine et de l'Orn8-oxytocine", Helv. Chim. Acta., 1963, 1669-1676 (Translation Included).
Jolley et al., "Terlipressin Infusion in Catecholamine-resistant Shock", *Anaesth. Intensive Care*, 2003, 31, 560-564.
Kimbrough et al., "lysine-vasotocin, a Synthetic Analogue of the Posterior Pituitary Hormones Containing the Ring of Oxytocin and the Side Chain of Lysine-vasopressin", *J. Biol. Chem.*, 1961, 236(3), 778-780.
Lauzier et al. "Utilisation de la vasopressine lors du traitement du choc septique; Vasopressin in the treatment of septic shock", *Reanimation*, 2004, 13, 147-153 (with English abstract).
Merrifield, "Solid Phase Peptide Synthesis. I. The Synthesis of a Tetrapeptide", *J. Am. Chem. Soc.*, 1963, 85, 2149-2154.
Mitsunobu, "The Use of Diethyl Azodicarboxylate and Triphenylphosphine in Synthesis and Transormation of Natural Products", *Synthesis*, 1981, 1-28.
Moreau et al. "Comparison of the effect of terlipressin and albumin on arterial blood volume in patients with cirrhosis and tense ascites treated by paracentesis: a randomised pilot study." *Gut.*, 2002, 50, 90-94.
Morelli et al. "Effects of terlipressin on systemic and regional haemodynamics in catecholamine-treated hyperkinetic septic shock", *Intensive Care Med.*, 2004, 30, 597-604.
O'Brien et al., "Terlipressin for norepinephrine-resistant septic shock", *The Lancet*, 2002, 359, 1209-1210.
Reid, I., "Role of Vasopressin Deficiency in the Vasodilation of Septic Shock", *Circulation*, 1997, 95, 1108-1110.
Schillinger et al., "Structure Activity Relationship if the Insulin-Like Effects of the Neurophysical Peptide Hormones", *Eur. J. Biochem.*, 1972, 27(3), 473-481.
Streitweiser et al., "Introduction to Organic Chemistry", $3^{rd}$ Ed., Macmillan Publishing Co., New York 1995, pp. 564-567.
Terrillon et al. "Synthesis and Characterization of Fluorescent Antagonists and Agonist for Human Oxytocin Vasopressin $V_{1a}$ Receptors", *J. Med. Chem.*, 2002, 45, 2579-2588.
Vilhardt et al., "Antidiuretic activity and release of Factor VIII by vasopressin analogues", *Eur. J. Pharmacol.*, 1993, 232, 223-226.
Wisniewski and Koiodziejczyk, "The efficient synthesis of FMOC-L-homoglutamine", *Oppi Briefs*, 1997, 29(3), 338-341.
Wold et al., "Principal property values for six non-natural amino acids and their application to a structure-activity relationship for oxytocin peptide analogues", *Can. J. Chem.*, 1987, 65(8), 1814-1820.
International Preliminary Report on Patentability and Written Opinion dated Feb. 13, 2007 for International Appln. No. PCT/US2005/027772 (4 pgs.).
International Search Report dated Mar. 3, 2008 for International Appln. No. PCT/US2007/003213 (3 pgs.).
International Search Report dated Dec. 13, 2005 for International Appln. No. PCT/US2005/027772 (1 pg.).
Derwent Abstract, AN2003-812511, XP-002312063, abstract of Kurasawa et al., WO2003/082334 (2003), 1 page.
Dohler et al.; "Wirkmechanismen der vasokonstriktiven Therapie der Osophagusvarizenblutung"; Zeitschrift Fur Gastroenterologie, vol. 41, 2003, pp. 1001-1016 (English abstract).
Kurasawa et al., "Exogenous Arginine Vasopression Increases Tear Fluid Secretion via Vasopressin $V_{1a}$ Receptors in Rats," *Invest Opthalmol Vis Sci.*, 2005, 46: E-Abstract 4407.
Mitchell et al., "Editorial II: Vasopressin and its antagonist: what are their roles in acute medical care?", *Br J Anaesthesia*, Aug. 2007, 99(2):154-158.
Peterson, "The Effect of Vasopressin and Related Compounds at Via and V2 Receptors in Animal Models Relevant to Human Disease." *Basic & Chemical Pharmacology & Technology.*, 2006,99:96-103.
Walter; "Therapie des hepatorenalen Syndroms"; Praxis, Schweizerische Rundschau Fur Medizin-Inhalt & Zusammenfassungen, vol. 86, No. 4,1997, Retrieved from the Internet on Jan. 10, 2008 URL:http://www.oraxis.ch/content/1997/04 1997.html> (English Abstracts included).
Wenzel et al., "A Comparison of Vasopressin and Epinephrine for Out-of-Hospital Cardiopulmonary Resuscitation," *N. Engl. J. Med.*, 2004, 350(2):105-113.
Wenzel et al., "Employing vasopressin during cardiopulmonary resuscitation and vasodilatory shock as a lifesaving vasopressor," *Cardiovasc. Res.*, 2001, 51:529-541.

* cited by examiner

COMPOUNDS

This application is the National Phase of PCT/US2007/003213, filed Feb. 5, 2007, which claims priority to U.S. Application No. 60/771,870, filed Feb. 10, 2006.

FIELD OF THE INVENTION

The present invention relates to novel compounds, pharmaceutical compositions comprising the same, use of said compounds for the manufacture of a medicament for treatment of inter alia shock conditions as well as to a method for treatment of said conditions, wherein said compounds are administered.

BACKGROUND

Peptidic vasopressin V1a receptor agonists, such as terlipressin, have recently (see e.g. O'Brian et al., Lancet 359 (9313):1209-10, Jun. 4, 2002) received increased attention for clinical use in treatment of critical care diseases and conditions, including shock of hypovolemic (e.g. hemorrhagic) or vasodilatory (e.g. septic) origin, bleeding esophageal varices (BEV), hepatorenal syndrome (HRS), cardiopulmonary resuscitation and anesthesia-induced hypotension. They have also been shown to have clinical use in the treatment of orthostatic hypotension, paracentesis-induced circulatory dysfunction, intra-operative blood loss and blood loss associated with burn debridement and epistaxis, and for treatment of various ocular diseases by increasing lacrimation/tear formation.

It is an objective of the present invention to provide efficacious compounds, especially at the human V1a (hV1a) receptor, that may provide alternatives, e.g., to terlipressin in the treatment of critical care conditions.

DISCLOSURE OF THE INVENTION

The present invention relates to compounds represented by the general formula (I):

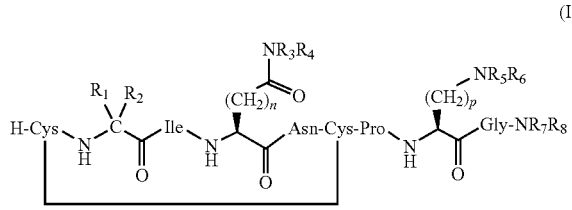

wherein:
$R_1$ is selected from H and part of an alicyclic structure that comprises from 3 to 8 carbon atoms;
$R_2$ is selected from $(CH_2)_m$—X and part of said alicyclic structure;
m is selected from 0, 1, 2 and 3;
n is selected from 0, 1, 2, 3 and 4;
p is selected from 2, 3 and 4;
when $R_1$ is H, $R_2$ is $(CH_2)_m$—X;
when $R_1$ is not H, $R_1$ and $R_2$ together with the a carbon atom to which they are attached form said alicyclic structure;
when m is 0, 2 or 3, X is selected from $C_{3-8}$-cycloalkyl, $C_{5-8}$-cycloalkenyl and $C_{5-8}$-cycloalkynyl;
when m is 1, X is selected from $C_{3-8}$-cycloalkyl, $C_{5-8}$-cycloalkenyl, $C_{5-8}$-cycloalkynyl, isopropyl and tert-butyl;
said alicyclic structure, $C_{3-8}$-cycloalkyl, $C_{5-8}$-cycloalkenyl and $C_{5-8}$-cycloalkynyl optionally have at least one alkyl, O-alkyl or hydroxyl substituent;
$R_3$, $R_4$, $R_5$, $R_6$, $R_7$ and $R_8$ are each independently selected from H, alkyl, OH, O-alkyl and OC(O)-alkyl;
alkyl is selected from $C_{1-6}$ straight and $C_{4-9}$ branched chain alkyl and optionally has at least one hydroxyl substituent; and
solvates and pharmaceutically acceptable salts thereof.

It deserves mentioning that e.g. also isopropyl and 2-n-butyl groups are encompassed by the expression $C_{1-6}$ straight chain alkyl, as said expression is not related to the binding site of the straight chain in question.

$C_{1-6}$ denotes having from one to six carbon atoms, including any number therebetween, and this nomenclature is used analogously herein.

The abbreviations used herein are:
AcBuc 1-aminocyclobutane-1-carboxylic acid
Ala(cPe) cyclopentylalanine
Boc tert-butoxycarbonyl
BOP benzotriazol-1-yloxy trisdimethylaminophosphonium hexafluorophosphate
Bu butyl
Cha cyclohexylalanine
Dbu 2,4-diaminobutyric acid
DCC N,N'-dicyclohexylcarbodiimide
DCHA dicyclohexylamine
DCM dichloromethane
DIAD diisopropyl diazodicarboxylate
DIC N,N'-diisopropylcarbodiimide
DIEA N,N-diisopropyl-N-ethylamine
DMF N,N-dimethylformamide
Fm 9-fluorenylmethyl
Fmoc 9-fluorenylmethoxycarbonyl
HOBt 1-hydroxybenzotriazole
HPLC high performance liquid chromatography
i iso
Mmt 4-methoxytrityl
Mob p-methoxybenzyl
MS mass spectrometry
Orn ornithine
Ph phenyl
Pr propyl
PyBOP benzotriazol-1-yloxy trispyrrolidinephosphonium hexafluorophosphate
o-NBS-Cl 2-nitrobenzenesulfonyl chloride
OT oxytocin
Rt retention time
t tert
TFA trifluoroacetic acid
TIS triisopropylsilane
TMOF trimethylorthoformate
TPP triphenylphosphine
Trt trityl
VT vasotocin, [Ile³]vasopressin
Z benzyloxycarbonyl Unless otherwise specified L-amino acids were used, and conventional amino acid terminology is adhered to.

Examples of pharmaceutically acceptable salts comprise acid addition salts, e.g. a salt formed by reaction with hydrohalogen acids, such as hydrochloric acid, and mineral acids, such as sulphuric acid, phosphoric acid and nitric acid, as well as aliphatic, alicyclic, aromatic or heterocyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, phydroxybenzoic acid, embonic acid, methanesulphonic acid, ethanesulphonic acid, hydroxyethanesulphonic acid, halobenzenesulphonic acid, toluenesulphonic acid and naphtalenesulphonic acid.

In preferred embodiments $R_7$ and $R_8$ are H. It is especially preferred that $R_3$ and $R_4$ are H.

It is also preferred that n is 1 or 2. Alkyl is typically selected from methyl, ethyl, n-propyl, i-propyl, t-butyl and i-amyl.

X is preferably selected from cyclopentyl and cyclohexyl.

Said alicyclic structure is preferably a cyclobutyl structure.

In the most preferred embodiment, said compound having the formula (I) is selected from a group consisting of:

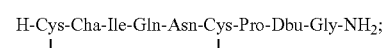

(Cmpd. 1)

(SEQ ID NO: 1)

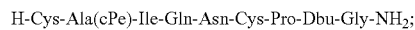

(Cmpd. 2)

(SEQ ID NO: 2)

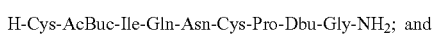

(Cmpd. 3)

(SEQ ID NO: 3)

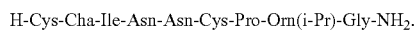

(Cmpd. 4)

(SEQ ID NO: 4)

The number in parenthesis denotes the compound as referred to in the following.

Furthermore the present invention relates to a compound as set forth above for use as a pharmaceutical.

Accordingly, the present invention also relates to a pharmaceutical composition comprising a compound as set forth above as active ingredient in association with a pharmaceutically acceptable adjuvant, diluent or carrier.

The pharmaceutical composition may be adapted for oral, intravenous, topical, intraperitoneal, nasal, buccal, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

It should be noted that the composition according to the present invention may optionally include two or more of the above outlined compounds.

The present pharmaceutical composition may optionally comprise e.g. at least one further additive selected from a disintegrating agent, binder, lubricant, flavoring agent, preservative, colorant and any mixture thereof. Examples of such and other additives are found in "*Handbook of Pharmaceutical Excipients*"; Ed. A. H. Kibbe, 3$^{rd}$ Ed., American Pharmaceutical Association, USA and Pharmaceutical Press UK, 2000.

The present pharmaceutical composition is most preferably adapted for parenteral administration. It may comprise a sterile aqueous preparation of the compounds of the invention preferably isotonic with the blood of the recipient. This aqueous preparation may be formulated according to known methods, using suitable dispersing or wetting agents and suspending agents. Illustrative of a preparation produced in such conventional fashion is the aqueous formulation, Remestype® (terlipressin). The preparation also may be a sterile injectable solution or suspension in a diluent or solvent, for example, as a solution in 1,3-butane diol. Water, Ringer's solution, and isotonic sodium chloride solution are exemplary acceptable diluents. Sterile, fixed oils may be employed as a solvent or suspending medium. Bland fixed oils, including synthetic mono or di-glycerides, and fatty acids, such as oleic acid, may also be used.

In addition, the present invention relates to use of a compound as outlined above for the manufacture of a medicament for treatment of shock of hypovolemic or vasodilatory origin, BEV, HRS, cardiopulmonary resuscitation, anesthesia-induced hypotension, orthostatic hypotension, paracentesis-induced circulatory dysfunction, intra-operative blood loss or blood loss associated with burn debridement and epistaxis, and for treatment of various ocular diseases by increasing lacrimation/tear formation.

In another embodiment the invention relates to a method for treatment of shock of hypovolemic or vasodilatory origin, BEV, HRS, cardiopulmonary resuscitation, anesthesia-induced hypotension, orthostatic hypotension, paracentesis-induced circulatory dysfunction, intra-operative blood loss or blood loss associated with burn dbridement and epistaxis, and of various ocular diseases by increasing lacrimation/tear formation, wherein said method comprises administering to an animal, including human, patient of a therapeutically effective amount of a compound as outlined above.

The typical dosage of the compounds according to the present invention varies within a wide range and will depend on various factors such as the individual needs of each patient and the route of administration. The dosage administered by infusion is generally within the range of 0.01-200 µg/kg body weight per hour. A physician of ordinary skill in the art will be able to optimise the dosage to the situation at hand.

Experimental (Synthesis)

Amino acid derivatives and resins were purchased from commercial providers (Novabiochem, Bachem, Peptide International and PepTech Corporation). Other chemicals and solvents were provided from Sigma-Aldrich, Fisher Scientific and VWR.

The compounds herein were synthesised by standard methods in solid phase peptide chemistry utilising both Fmoc and Boc methodology. Unless otherwise provided, all reactions were performed at room temperature. In addition to the references cited supra, the following standard reference literature provides further guidance on general experimental set up, as well as on the availability of required starting material and reagents:

Kates, S. A., Albericio, F., Eds., *Solid Phase Synthesis. A Practical Guide*, Marcel Dekker, New York, Basel, 2000;

Stewart, J. M., Young, J. D. *Solid Phase Synthesis, Pierce Chemical Company*, 1984;

Bisello, et al., *J. Biol. Chem.* 1998, 273, 22498-22505; and

Merrifield, *J. Am. Chem. Soc.* 1963, 85, 2149-2154.

Purity of the synthesized peptide may be determined by analytical reversed phase HPLC. Structural integrity of the peptides may be confirmed using amino acid analysis and electrospray mass spectrometry.

The peptides synthesised by Fmoc methodology were cleaved with a TFA/TIS/H$_2$O 96/2/2 (v/v/v) solution, and cleavage in Boc methodology was accomplished with 90% HF/10% anisole (v/v) solution. Disulfide bridge (ring) formation was achieved by oxidation of linear peptides dissolved in 10% TFA (aq) with iodine. Peptides were purified by preparative HPLC in triethylammonium phosphate buffers (aq). The compounds were finally converted to acetate salts using conventional HPLC methodology. The fractions with a purity exceeding 97% were pooled and lyophilised.

Synthesis of peptides with alkylated side chain in position no. 8 (e.g. compound 4):

The peptides were assembled with Fmoc methodology.

The diamino acid residue in position no. 8 was introduced with an acid labile (i.e. removable with a solution containing 1-2% TFA) protecting group, such as methoxytrityl (Mmt; see Barlos, K. et al. in *Peptides* 1992, Schneider, C. H., Eberle, A. N., Eds., ESCOM Science Publishers B. V., 1993, pp 283-284). Resin bound peptide was treated with a DCM/TIS/TFA 93/5/2 (v/V/V) solution for the Mmt group removal. Reductive alkylation with acetone/NaBH(OAc)$_3$ provided the N-isopropyl peptide.

To avoid undesirable N,N-dialkylation in reductive alkylation in the above procedure, which may occur when straight chain alkyl aldehydes are used, an alternative was developed, wherein after the Mmt removal the amino group was first derivatised with 2-nitrobenzenesulfonyl chloride (o-NBS-Cl; see Fukuyama, T.; Jow, C.-K.; Cheung, M. *Tetrahedron Lett.* 1995, 36, 6373-6374). The resulting sulphonamide was then alkylated with an appropriate alcohol under conventional Mitsunobu reaction conditions, typically utilising TPP/DIAD in 1,2-dimethoxyethane (Mitsunobu, O. *Synthesis* 1981, 1-28). The o-NBS-Cl group was subsequently removed with 5% potassium thiophenolate in DMF, after which the peptide was cleaved from the resin.

Synthesis of peptides with N-alkylated side chain in position no. 4:

The peptides were assembled with Boc methodology.

The residue in position no. 4 was introduced in the sequence as Boc-Asp(OFm)-OH. After complete peptide assembly the side chain protection was removed with 30% piperidine in DMF. The resulting free carboxylic group was converted to the desired amide by coupling with an appropriate amine mediated by PyBOP or BOP/DIEA. The N-terminal Boc group was then removed, followed by HF cleavage, cyclisation and purification by HPLC.

Table 1 lists the compounds prepared by the above procedure together with the determined (vide infra) EC$_{50}$ (median effective concentration) expressed in nanomol/L. R$_3$, R$_4$, R$_5$, R$_6$, R$_7$ and R$_8$ are H for all compounds except compound 4, where R$_6$ is isopropyl instead of H. For the listed compounds m is 1, except where R$_1$ and R$_2$ are part of an alicyclic structure (formed together with the α carbon of the amino acid in position no. 2) exemplified here as 1,1-cyclobutyl.

TABLE 1

Compounds prepared with the formula (I)

| R$_1$ | R$_2$ | X | n | p | EC$_{50}$ | Denoted |
|---|---|---|---|---|---|---|
| H | CH$_2$X | cyclohexyl | 2 | 2 | 0.27 | compound 1 (SEQ ID NO: 1) |
| H | CH$_2$X | cyclopentyl | 2 | 2 | 0.80 | compound 2 (SEQ ID NO: 2) |
| 1,1-cyclobutyl | — | | 2 | 2 | 0.94 | compound 3 (SEQ ID NO: 3) |
| H | CH$_2$X | t-butyl | 2 | 2 | 10.7 | compound 5 (SEQ ID NO: 5) |
| H | CH$_2$X | i-propyl | 2 | 2 | 12.0 | compound 6 (SEQ ID NO: 6) |
| 1,1-cyclobutyl | — | | 1 | 3 | 7.93 | compound 7 (SEQ ID NO: 7) |
| H | CH$_2$X | cyclopentyl | 1 | 3 | 7.70 | compound 8 (SEQ ID NO: 8) |
| H | CH$_2$X | cyclohexyl | 1 | 3 | 0.75 | compound 4 (SEQ ID NO: 4) |
| 1,1-cyclobutyl | — | | 1 | 2 | 14.8 | compound 9 (SEQ ID NO: 9) |
| H | CH$_2$X | cyclopentyl | 1 | 2 | 17.8 | compound 10 (SEQ ID NO: 10) |
| H | CH$_2$X | cyclohexyl | 1 | 3 | 9.93 | compound 11 (SEQ ID NO: 11) |
| H | CH$_2$X | cyclohexyl | 1 | 2 | 2.28 | compound 12 (SEQ ID NO: 12) |
| N/A | | | | | 82.1 | terlipressin |

The following detailed examples are provided to further illustrate the synthesis:

Compound 4; [Cha$^2$, Asn$^4$, Orn(i-Pr)$^6$]VT:

The amino acid derivatives used were Boc-Cys(Trt)-OH, Fmoc-Cha-OH, Fmoc-Ile-OH, Fmoc-Gln(Trt)-OH, Fmoc-Asn(Trt)-OH, Fmoc-Cys(Trt)-OH, Fmoc-Pro-OH, Fmoc-Orn(Mmt)-OH and Fmoc-Gly-OH. Analytical HPLC was performed on a Waters 600 Liquid Chromatograph using a Vydac C18, 5μ 4.6×250 mm, column at a flow rate of 2 ml/min. Preparative HPLC was performed on a Waters 2000 Liquid Chromatograph using a Prepak 47×300 mm cartridge at a flow rate of 100 ml/min. Final compound analysis was performed on a 1100 Agilent Liquid Chromatograph using a Vydac C18, 5μ 2.1×250 mm, column at a flow rate of 0.3 ml/min. Mass spectra were recorded on a Finnigan MAT spectrometer.

The fully protected peptide resin was synthesised on an Applied Biosystems 9050 Peptide Synthesiser starting from 0.4 g (0.1 mmol) of Tentagel-S-RAM resin (Peptides International). DIC/HOBt mediated single couplings with a 4-fold excess of amino acid derivatives were performed. The Fmoc group was removed with 20% piperidine in DMF. Upon completion of the automated synthesis, the resin was transferred into a manual synthesis vessel and was treated with DCM/TIS/TFA 93/5/2 (v/v/v) solution (30 ml) for 2×1.5 hours for removal of the Mmt group. The resin was thoroughly washed with DCM and was subsequently suspended in 15 ml of 1,2-dichloroetehane/TMOF 1:1 (v/v). 0.2 ml of acetone was then added followed by 0.6 g of NaBH(OAc)$_3$. The suspension was shaken overnight and the resin was washed with methanol, DMF and DCM and dried in vacuo. The resin was then treated with 30 ml of the TFA/TIS/H$_2$O 96/2/2 (v/v/v) solution for 1.5 hours and filtered off. The filtrate was evaporated and the crude linear peptide was precipitated with diethyl ether. The precipitate was immediately dissolved in 500 ml of 10% TFA (aq), and the peptide was oxidised by adding 0.1 M I$_2$ in methanol to the magnetically stirred solution until yellow color persisted. Excess of iodine was reduced with ascorbic acid. The reaction mixture was then cooled with crushed ice and pH was adjusted to about 5 by adding concentrated ammonia (aq). The mixture was loaded onto an HPLC column and purified using a triethylammonium phosphate buffer with pH 5.2. The compound was eluted with a gradient of acetonitrile. The fractions with a purity exceeding 97% were pooled, and the resulting solution was diluted with 2 volumes of water. The solution was reloaded onto the column which was then washed with 2 l of 0.1 M ammonium acetate (aq) and equilibrated with 2% acetic acid (aq). The compound was eluted with a fast (3%/min) gradient of acetonitrile. The fractions containing the desired product were pooled and lyophilised. 20.7 mg (20% yield) of white amorphous powder was obtained. HPLC: Rt=8.2 min, gradient: 30>50% B over 20 min, flow: 0.3 ml/min, t=40° C., solvent A 0.01% TFA (aq), solvent B 70% CH$_3$CN, 0.01% TFA (aq); Purity: 100%; MS (M+H$^+$): expected 1026.5, observed 1026-5.

Compound 3; [AcBuc$^2$, Dbu$^8$]VT :

The amino acid derivatives used were Boc-Cys(Mob)OH, Boc-AcBuc-OH, Boc-11e-OH, Boc-Gln-OH, Boc-Asn-OH, Boc-Pro-OH, Boc-Dbu(Z)-OH DCHA salt and Boc-Gly-OH, all purchased from Novabiochem and Bachem. HPLC and MS operations were performed as in the synthesis of compound 4.

The fully protected peptide resin was manually synthesised starting from 0.6 g (0.4 mmol) of 4-methylbenzhydrylamine resin (Novabiochem). DCC, PyBOP or DIC/HOBt mediated single couplings with 2.5-fold excess of amino acid derivatives were employed. The Boc group was removed with 50% TFA in DCM containing 1% of m-cresol. The finished resin was washed with methanol, DMF and DCM and dried in vacuo. The peptide was cleaved from the resin by using 30 ml of anhydrous HF containing 3 ml of anisole at 0° C. for 90 minutes. The HF was evaporated off, and the crude linear peptide was washed with diethyl ether. The peptide was immediately dissolved in 200 ml of 25% acetonitrile/10% TFA (aq) and oxidised as described supra. The resulting mixture was loaded directly onto an HPLC column and purified using triethylammonium phosphate buffer at pH 2.3. Unless otherwise provided the subsequent steps were identical to the procedure for compound 4. 80.6 mg (22% yield) of white amorphous powder was obtained. HPLC: R$_t$=7.3 min, gradient: 20→40% B over 20 min, flow: 0.3 ml/min, t=40° C., solvent A 0.01% TFA (aq), solvent B 70% CH$_3$CN, 0.01% TFA (aq); Purity: 99.6%; MS (M+H$^+$): expected 928.4, observed 928.3.

The other compounds were prepared by analogous variation of these synthetic procedures.

Experimental (Biological Testing)

In vitro receptor assay:

Agonist activity of compounds on the hV1a receptor was determined in a transcriptional reporter assay by transiently transfecting a hV1a receptor expression DNA into HEK-293 cells in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells were exposed to serial dilutions of compounds diluted 10-fold per dose for 5 hours, followed by lysis of cells, determination of luciferace activity, and determination of compound efficacies and EC$_{50}$ values through non-linear regression. Arginine-vasopressin (AVP) was used as an internal control in each experiment (EC$_{50}$=0.21 nM), and compounds were tested in at least three independent experiments.

The results of the in vitro assays are depicted in table 1 supra, including results for terlipressin. The EC$_{50}$ value given is the geometric mean expressed in nanomol/L (nM).

All references listed are to be regarded as an integral part of the present writ.

---

The invention claimed is:

1. A compound having the formula (I):

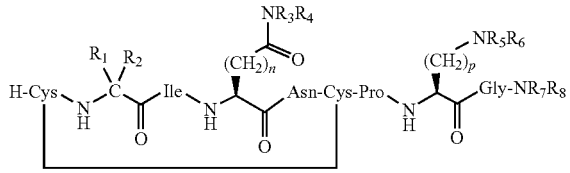

wherein:
R₁ is H; and
R₂ is (CH₂)$_m$—X;
or R₁ and R₂ in combination with the carbon atom to which they are attached together form an acyclic structure that comprises from 3 to 8 carbon atoms;
m is selected from 0, 1, 2 and 3;
n is selected from 0, 1, 2, 3 and 4;
p is selected from 2, 3 and 4;
when m is 0, 2 or 3, X is selected from C$_{3-8}$-cycloalkyl and C$_{5-8}$-cycloalkenyl;
when m is 1, X is selected from C$_{3-8}$-cycloalkyl, C$_{5-8}$-cycloalkenyl, isopropyl and tert-butyl;
said alicyclic structure, C$_{3-8}$-cycloalkyl, and C$_{5-8}$-cycloalkenyl, optionally have at least one alkyl, O-alkyl or hydroxyl substituent; and
R₃, R₄, R₅, R₆, R₇ and R₈ are each independently selected from H, alkyl, OH, O-alkyl and OC(O)-alkyl;
wherein each alkyl is selected from C$_{1-6}$ straight and C$_{4-8}$ branched chain alkyl groups and optionally has at least one hydroxyl substituent;
or a pharmaceutically acceptable salt thereof.

2. A compound or pharmaceutical salt thereof according to claim 1, wherein R₇ and R₈ are H.

3. A compound or pharmaceutical salt thereof according to claim 1, wherein R₃ and R₄ are H.

4. A compound or pharmaceutical salt thereof according to claim 1, wherein n is 1 or 2.

5. A compound or pharmaceutical salt thereof according to claim 1, wherein each alkyl is selected from methyl, ethyl, n-propyl, i-propyl, t-butyl and i-amyl.

6. A compound or pharmaceutical salt thereof according to claim 1, wherein X is cyclopentyl or cyclohexyl.

7. A compound or pharmaceutical salt thereof according to claim 1, wherein said alicyclic structure is a cyclobutyl structure.

8. A pharmaceutical composition comprising a compound or pharmaceutically acceptable salt thereof according to claim 1 and a pharmaceutically acceptable adjuvant, diluent or carrier.

9. A compound or pharmaceutical salt thereof according to claim 1, wherein the compound is a compound of the following formula:

(SEQ ID NO: 1)

H-Cys-Cha-Ile-Gln-Asn-Cys-Pro-Dbu-Gly-NH₂.

10. A compound or pharmaceutically acceptable salt thereof according to claim 1, wherein the compound is a compound of the following formula:

(SEQ ID NO: 2)

H-Cys-Ala(cPe-Ile-Gln-Asn-Cys-Pro-Dbu-Gly-NH₂.

11. A compound or pharmaceutically acceptable salt thereof according to claim 1, wherein the compound is a compound of the following formula:

(SEQ ID NO: 3)

H-Cys-AcBuc-Ile-Gln-Asn-Cys-Pro-Dbu-Gly-NH₂.

12. A compound or pharmaceutically acceptable salt thereof according to claim 1, wherein the compound is a compound of the following formula:

(SEQ ID NO: 4)

H-Cys-Cha-Ile-Asn-Asn-Cys-Pro-Orn (i-Pr) -Gly-NH₂.

13. A compound or pharmaceutically acceptable salt thereof according to claim 1, wherein:
R₃ and R₄ are H;
R₇ and R₈ are H;
n is 1 or 2;
each alkyl is selected from methyl, ethyl, n-propyl, i-propyl, t-butyl and i-amyl;
X is cyclopentyl or cyclohexyl; and
said alicyclic structure is a cyclobutyl structure.

14. A method for treatment of a condition selected from:
shock of hypovolemic origin;
shock of vasodilatory origin;
bleeding esophageal varices;
hepatorenal syndrome;
anesthesia-induced hypotension;
orthostatic hypotension;
paracentesis-induced circulatory dysfunction;
intra-operative blood loss;
blood loss associated with burn debridement; and
blood loss associated with epistaxis;
wherein said method comprises administering to an animal patient in need of such treatment a therapeutically effective amount of a compound or pharmaceutically acceptable salt thereof according to claim 1.

15. The method of claim 14, wherein said animal patient is a human.

16. A method of treatment comprising administering to an animal patient in need of cardiopulmonary resuscitation a therapeutically effective amount of a compound or pharmaceutically acceptable salt thereof according to claim 1.

17. The method of claim 16, wherein said animal patient is a human.

18. A method of treatment comprising administering to an animal patient in need of treatment of an ocular disease by increasing lacrimation or tear formation a therapeutically effective amount of a compound or pharmaceutically acceptable salt thereof according to claim 1.

19. The method of claim 18, wherein said animal patient is a human.

* * * * *

UNITED STATES PATENT AND TRADEMARK OFFICE
CERTIFICATE OF CORRECTION

| | | |
|---|---|---|
| PATENT NO. | : 8,883,965 B2 | Page 1 of 1 |
| APPLICATION NO. | : 12/223654 | |
| DATED | : November 11, 2014 | |
| INVENTOR(S) | : Kazimierz Wisniewski and Robert Galyean | |

It is certified that error appears in the above-identified patent and that said Letters Patent is hereby corrected as shown below:

On the title page, item 56

Column 2, line 13 (Other Publications); delete "efiled" and insert -- filed --.

Page 2, column 1, line 33 (Other Publications); delete "Seach" and insert -- Search --.

Page 2, column 2, line 2 (Other Publications); delete "Transormation" and insert -- Transformation --.

Page 2, column 2, line 52 (Other Publications); delete "Syndroms";" and insert -- Syndromes"; --.

In the claims

Column 16, line 2; In claim 10, delete; " H-Cys-Ala(cPe-Ile-Gln-Asn-Cys-Pro-Dbu-Gly-NH$_2$. " and insert -- H-Cys-Ala(cPe)-Ile-Gln-Asn-Cys-Pro-Dbu-Gly-NH$_2$ --.

Signed and Sealed this
Tenth Day of May, 2016

Michelle K. Lee
*Director of the United States Patent and Trademark Office*

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 1

Cys Xaa Ile Gln Asn Cys Pro Xaa Gly
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclopentylpropanoic acid
<220> FEATURE:
<221> NAME/KEY: MOD_RES
```

```
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 2

Cys Xaa Ile Gln Asn Cys Pro Xaa Gly
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 1-aminocyclobutanecarboxylic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 3

Cys Xaa Ile Gln Asn Cys Pro Xaa Gly
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: MOD_RES
<222> LOCATION: 8
<223> OTHER INFORMATION: Xaa = 2-amino-5-(isopropylamino)pentanoic acid
<220> FEATURE:
<221> NAME/KEY: DISULFID
<222> LOCATION: (1)...(6)

<400> SEQUENCE: 4

Cys Xaa Ile Asn Asn Cys Pro Xaa Gly
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-4,4-dimethylpentanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 5
```

```
Cys Xaa Ile Gln Asn Cys Pro Xaa Gly
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 6

Cys Leu Ile Gln Asn Cys Pro Xaa Gly
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 1-aminocyclobutanecarboxylic acid
<220> FEATURE:
<221> NAME/KEY: DISULFID
<222> LOCATION: (1)...(6)

<400> SEQUENCE: 7

Cys Xaa Ile Asn Asn Cys Pro Gly
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclopentylpropanoic acid
<220> FEATURE:
<221> NAME/KEY: DISULFID
<222> LOCATION: (1)...(6)

<400> SEQUENCE: 8

Cys Xaa Ile Asn Asn Cys Pro Gly
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 1-aminocyclobutanecarboxylic acid
<220> FEATURE:
<221> NAME/KEY: MOD_RES
```

-continued

```
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 9

Cys Xaa Ile Gln Asn Cys Pro Xaa Gly
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclopentylpropanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 10

Cys Xaa Ile Asn Asn Cys Pro Xaa Gly
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: DISULFID
<222> LOCATION: (1)...(6)

<400> SEQUENCE: 11

Cys Xaa Ile Asn Asn Cys Pro Gly
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 12

Cys Xaa Ile Gln Asn Cys Pro Xaa Gly
1               5
```